US00PP07781P

United States Patent [19]

van Andel

[11] Patent Number: Plant 7,781

[45] Date of Patent: Feb. 4, 1992

[54] CARNATION NAMED STACORPI

[75] Inventor: Jacob van Andel, Aalsmeer, Netherlands

[73] Assignee: Van Staaveren B.V., Netherlands

[21] Appl. No.: 578,471

[22] Filed: Sep. 7, 1990

[51] Int. Cl.[5] ..... A01H 5/00

[52] U.S. Cl. ..... Plt./71

[58] Field of Search ..... Plt./70, 71, 72

[56] References Cited

U.S. PATENT DOCUMENTS

P.P. 6,275 9/1988 Barberet et al. ..... Plt. 71

P.P. 6,290 9/1988 van Andel ..... Plt. 71

*Primary Examiner*—Howard J. Locker

*Attorney, Agent, or Firm*—Charles W. Rummler

[57] ABSTRACT

A new and original carnation cultivar particularly distinguished by the dawn pink coloration of its large blossoms, which are produced continuously during the Spring, Summer, Fall, and Winter blooming periods on a plant which has a strong and vigorous growth habit and a height of about 60 cm.

1 Drawing Sheet

BACKGROUND OF THE NEW PLANT

This new carnation cultivar originated as a sport discovered by me in 1987 at our nursery in Aalsmeer, Holland. This particular sport was selected for propagation because of its unusual dawn pink coloration and the overall high quality of its apparent growth habit. Asexual propagation of this selected plant was done by means of cuttings under my direction at Aalsmeer and propagation of this new plant by cuttings continued from generation to generation to determine whether the novel characteristics of the selected seedling would hold true from generation to generation so that its homogeneity could be assured.

This proved to be successful and this new carnation variety is now being propagated at Aalsmeer.

DESCRIPTION OF THE DRAWING

My new carnation cultivar is illustrated by the accompanying photographic drawing, which shows blooming portions of flower stems with the flowers shown in full development, the color rendition being as nearly true to that herein specified as is reasonably possible to obtain by professional photographic procedures.

DESCRIPTION OF THE NEW PLANT

The following is a detailed description of my new carnation variety based upon observation of plants grown in greenhouse as well as outdoors at Aalsmeer and blooming during the current year. The color designations stated herein are according to the R.H.S. Colour Chart published by The Royal Horticultural Society of London, England.

THE PLANT

Origin: Sport.

Parentage:

*Parent.*—Stacor (U.S. Plant Pat. No. 6,290).

Classification:

*Botanic.*—*Dianthus caryophyllus.*

*Commercial.*—Standard carnation.

Form: Tall, vigorous bush.

Height: 60 cm, in average, at first flush. Thereafter, the height increases with age.

Main stem:

*Length.*—About 60 cm, increasing with age.

*Growth.*—Vigorous and strong.

*Branching character.*—One side shoot at each node.

Foliage:

*Number of leaves.*—Varies with season or the amount of daylight.

*Leaf size.*—Normal.

*Leaf shape.*—Narrow, slightly curled. Margins: Entire. Texture: Leathery. Color: Both upper and under side are gray-green.

THE BUD

Size: Medium.

*Diameter.*—Averaging about 2 cm.

*Length.*—Averaging about 3 cm.

Shape: Columnar.

Calyx:

*Shape.*—Columnar.

*Size.*—Averaging about 17 mm in width and 30 mm in length.

*Splitting.*—The calyx rarely splits.

*Aspect.*—Smooth.

Flower stem:

*Character.*—Sturdy and erect.

*Color.*—Gray-green.

*Length.*—Averaging about 60 cm.

THE FLOWER

Blooming habit: Continuous, blooming the year around.

Size of flower: Large.

*Diameter.*—Averaging about 8 cm.

*Depth.*—Averaging about 3 cm.

Borne: Singly.

Shape:

*When first opening.*—High center.

*When mature.*—Dome-shaped.

Petalage:

*Number of petals.*—About 45.

*Texture.*—Smooth.

*Appearance.*—Satiny.

*Color.*—Both outer and inside petals: Body: 49 A. Base: 49 A. Reverse side: 49 A.

Flower stem:

*Length.*—Averaging about 60 cm.

*Character.*—Strong and upright.

Discoloration:

*After full bloom.*—Color turns to paler pink.

Persistence: The flowers hang on and dry.

Disease resistance: Resistant to *Fusarium oxysporum.*

Lasting quality: Averaging about 10 days as a cut flower and 18 days on the plant.

REPRODUCTIVE ORGANS

Stamens:

*Number.*—Few — approximately 3-8.

*Arrangement.*—Petaloid.

*Anthers.*—Size: Normal. Color: White with pink tops.

*Filaments.*—Length: 5 to 30 mm, in average. Color: 155 B.

*Pollen.*—Color: 27 A.

Pistils:

*Number.*—1.

*Styles.*—Length: About 20 mm. Color: 49 D.

Stigmas.—Color: 189 A/D.

FRUIT

Fertility: The fruit is fertile.

Shape: Conical.

Color at maturity: Light brown.

I claim:

1. The new and distinctive carnation cultivar, substantially as herein shown and described, particularly characterized by the dawn pink coloration of its continuously blooming flowers, which are borne singly on strong, upright stems of medium length.

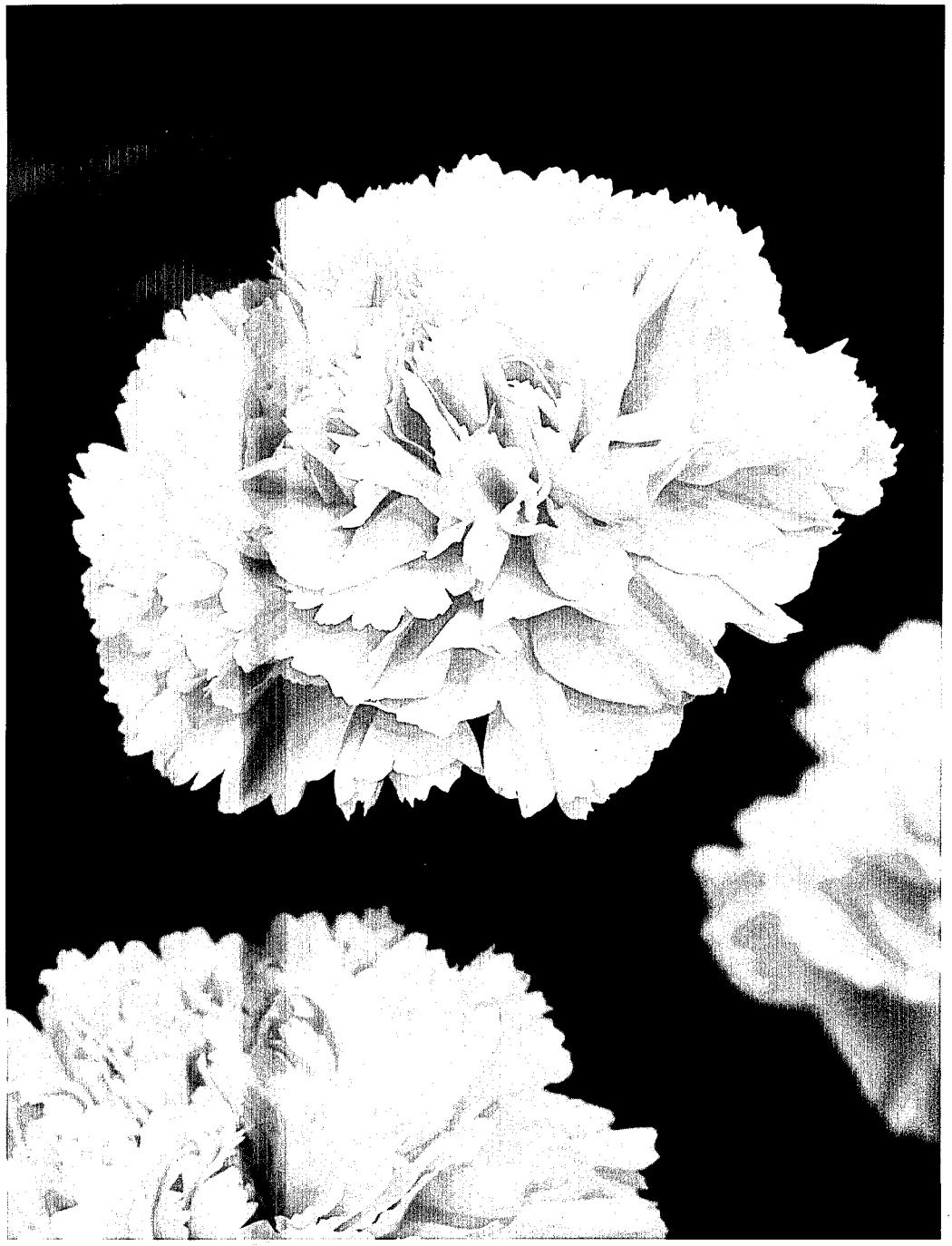

* * * * *